US007619646B2

(12) United States Patent
Freifeld et al.

(10) Patent No.: US 7,619,646 B2
(45) Date of Patent: Nov. 17, 2009

(54) SYSTEM AND METHOD TO ILLUMINATE AND IMAGE THE INSIDE DIAMETER OF A STENT

(75) Inventors: Daniel Freifeld, Napa, CA (US); John B. Burnett, Vacaville, CA (US)

(73) Assignee: Visicon Inspection Technologies LLC, Napa, CA (US)

( * ) Notice: Subject to any disclaimer, the term of this patent is extended or adjusted under 35 U.S.C. 154(b) by 0 days.

(21) Appl. No.: 11/714,447

(22) Filed: Mar. 6, 2007

(65) Prior Publication Data

US 2007/0219615 A1 Sep. 20, 2007

Related U.S. Application Data

(60) Provisional application No. 60/780,763, filed on Mar. 9, 2006.

(51) Int. Cl.
*H04N 7/18* (2006.01)
(52) U.S. Cl. .............................. 348/85; 348/64; 348/82; 382/152; 382/141; 356/241.1; 356/237.6
(58) Field of Classification Search .................. 348/85, 348/82, 64; 382/152, 141; 356/241.1, 237.6
See application file for complete search history.

(56) References Cited

U.S. PATENT DOCUMENTS

| 6,606,403 | B2* | 8/2003 | Freifeld | 382/152 |
| 6,697,102 | B1* | 2/2004 | Olsson et al. | 348/85 |
| 7,355,700 | B2* | 4/2008 | Kreckel et al. | 356/300 |

FOREIGN PATENT DOCUMENTS

| DE | 20 2005 013 876 | 1/2006 |
| JP | 2001-066521 | 3/2001 |
| JP | 2001-070455 | 3/2001 |
| JP | 2001-074433 | 3/2001 |

OTHER PUBLICATIONS

Laird, "Optical Scanning Tool Performs 100% Stent Inspection," *Medical Product Manufacturing News*, Nov. 2003.

* cited by examiner

*Primary Examiner*—Shawn An
(74) *Attorney, Agent, or Firm*—Wiggin and Dana LLP; Gregory S. Rosenblatt

(57) ABSTRACT

An optical system is effective to illuminate and scan an interior wall of an object having an interior bore, such as a stent. The system includes a light source, an object support having a light conducting portion, an image taking lens, and a line scan camera. The interior bore and the light conducting portion of the object support are in axial alignment with a center optical axis of the image taking lens. A drive mechanism engages the object without impacting the axial alignment. Various aspect of this optical system include a rotating wheel or transparent plate as the drive mechanism. The object support may be an opaque rod having a light conducting portion or a transparent rod. Electronics associated with this optical system include a rotary encoder engaging the drive system to drive an electric circuit capable of triggering the line scan camera in response to rotation of the object, thereby building a line by line image of the interior bore and the line scan camera connected to a computer-based imaging system effective to identify cosmetic and functional manufacturing defects.

7 Claims, 6 Drawing Sheets

SYSTEM AND METHOD TO ILLUMINATE AND IMAGE THE INSIDE DIAMETER OF A STENT

CROSS REFERENCE TO RELATED APPLICATION(S)

This patent application claims priority to U.S. Provisional Patent Application Ser. No. 60/780,763 titled "Method to Illuminate and Image the Inside Diameter of a Stent" that was filed on Mar. 9, 2006. That provisional patent application is incorporated by reference in its entirety herein.

U.S. GOVERNMENT RIGHTS

N.A.

BACKGROUND OF THE INVENTION

1. Field of the Invention

This invention relates to scanning and illuminating systems and methods for automated optical inspection. More particularly, to systems and methods to illuminate and inspect the inner bore of a stent or other tubular or conical device having an interior bore, where the interior bore may be either a through hole or a blind bore.

2. Description of Related Art

Stents are small wire mesh tubes used to hold open compromised arteries and other fluid conduits within a human body. The critical use of these devices and their small size requires stents to be manufactured to the highest possible quality standards.

Balloon expandable stents are vulnerable to failure during deployment. A sharp edge may puncture the balloon under high pressure causing a deployment failure. Also, arteries and vessels in the body flex and bend and a deployed stent must conform. Manufacturing defects may cause a point of weakness in the stent that is vulnerable to fatigue and failure as this point of weakness is repetitively bent or flexed in the vessel. Still further, if a portion of the stent breaks off and travels through the bloodstream, the patient is a risk of a stroke if this broken piece travels to the brain and lodges in an artery.

In view of the potential for catastrophic failure, rigorous inspection of the stent is required prior to deployment. Within the industry, visual inspection of stents has historically been done by human operators utilizing a microscope at 40× to 80× magnification. The stents are typically placed between two rollers and rotated under the microscopes while the human operator observes. An automated inspection system for measuring the dimensions of a stent and inspecting exterior surfaces is disclosed in U.S. Pat. No. 6,606,403, "Repetitive Inspection System with Intelligent Tools," that is incorporated by reference in its entirety herein.

Summarizing the current state of the art and its deficiencies, to achieve an automated method for inspection, a complete image of the stent needs to be quickly taken in good focus with clear contrast. The current state of the art is to use a stereomicroscope such as the Olympus SZ40 and ringlight. The stent is placed between two rollers and manually rotated. Illumination is provided from above with a fiber optic ringlight. While a video camera can be used with such a microscope, as the stent rotates between the rollers it does not always turn smoothly so it can move in and out of focus. Human operators often readjust the focus knob of the microscope to accommodate this, but this would be difficult and time consuming for an automatic method. As such, systems and methods need to be developed to rotate the stent in a well-defined and fixed geometry so as to always keep the stent in focus.

Further video cameras that can be used in conjunction with microscopes generally can only bring a very small section of the stent in focus at one time. To image every section of the stent with such an approach would require a very large number of individual images. This would be impractically time consuming to generate. Thus a method is required to generate a complete image of the inside diameter of the stent in just a few seconds. The current state of the art also uses a ringlight that illuminates the top outer diameter of the stent as well as the inner diameter thus creating a confusing image with excess glare.

There remains a need for an automated system and method to illuminate and image the inner bore of a stent and thereby facilitate the inspection of that inner bore.

BRIEF SUMMARY OF THE INVENTION

One embodiment of the invention is directed to an optical system that is effective to illuminate and scan an interior wall of an object having an interior bore. This system includes a light source, an object support having a light conducting portion, an image taking lens, and a line scan camera. The interior bore and the light conducting portion of the object support are in axial alignment with a center optical axis of the image taking lens. A drive mechanism engages the object without impacting the axial alignment.

Various aspect of this optical system include a rotating wheel or transparent plate as the drive mechanism. The object support may be an opaque rod having a light conducting portion or a transparent rod. Electronics associated with this optical system include a rotary encoder engaging the drive system to drive an electric circuit capable of triggering the line scan camera in response to rotation of the object, thereby building a line by line image of the interior bore and the line scan camera connected to a computer-based imaging system effective to identify cosmetic and functional manufacturing defects.

One use for the optical system is to illuminate and inspect stents.

The details of one or more embodiments of the invention are set forth in the accompanying drawings and the description below. Other features, objects and advantages of the invention will be apparent from the description and drawings, and from the claims.

DESCRIPTION OF THE INVENTION

One embodiment of the invention utilizes a linear array camera, larger area taking lens with relatively shallow depth of field, and a drive device to rotate a stent in a fixed location in space so as to keep the inner diameter clearly in focus across the field of view. This taking lens preferably is effective to image a substantial portion of the stent along its axial length, typically 10 mm or more. An encoder is affixed to the rotary drive device and is used to trigger the camera. An illumination source is geometrically configured to avoid putting light on an upper outer diameter of the part. The numerical aperture of the taking lens is at least as large as that of current manual microscopes (NA=0.1 or higher) for the purpose of bringing the outer diameter out of focus while the inner diameter is in sharp focus. The result of this optical configuration is a flat unrolled image of the stent inner diameter. This image is then analyzed for quality using grayscale image processing techniques available on an image processing board such as the Odyssey from Matrox Imaging, Montreal, Canada.

One aspect of this embodiment is that the drive device effectively rotates the stent while providing an unobstructed view of the stent inner diameter. A number of different methods for this are described. One method is to mount the stent on a clear rod or tube and use a correcting cylindrical optical element to reverse any optical distortion caused by the rod or tube. Another method is to mount the stent on a slotted metal rod and propel it around this rod by a compliant roller or slide mechanism. The camera can then image the inner diameter of the stent by viewing through this slot. To improve the image, if the drive mechanism is partially transparent or translucent, illumination can be sent up through the drive mechanism and light reflected off a portion of the slotted rod. This approach achieves the desired goal of illuminating only the inner diameter of the stent and not the outer diameter.

Another embodiment is to capture the stent firmly against two rollers with a third roller or with a clear plate that moves synchronously with the rotating stent. Two of the rollers could be used as reflectors to direct light to the ID of the stent without hitting the outer diameter surface.

Figure 1:
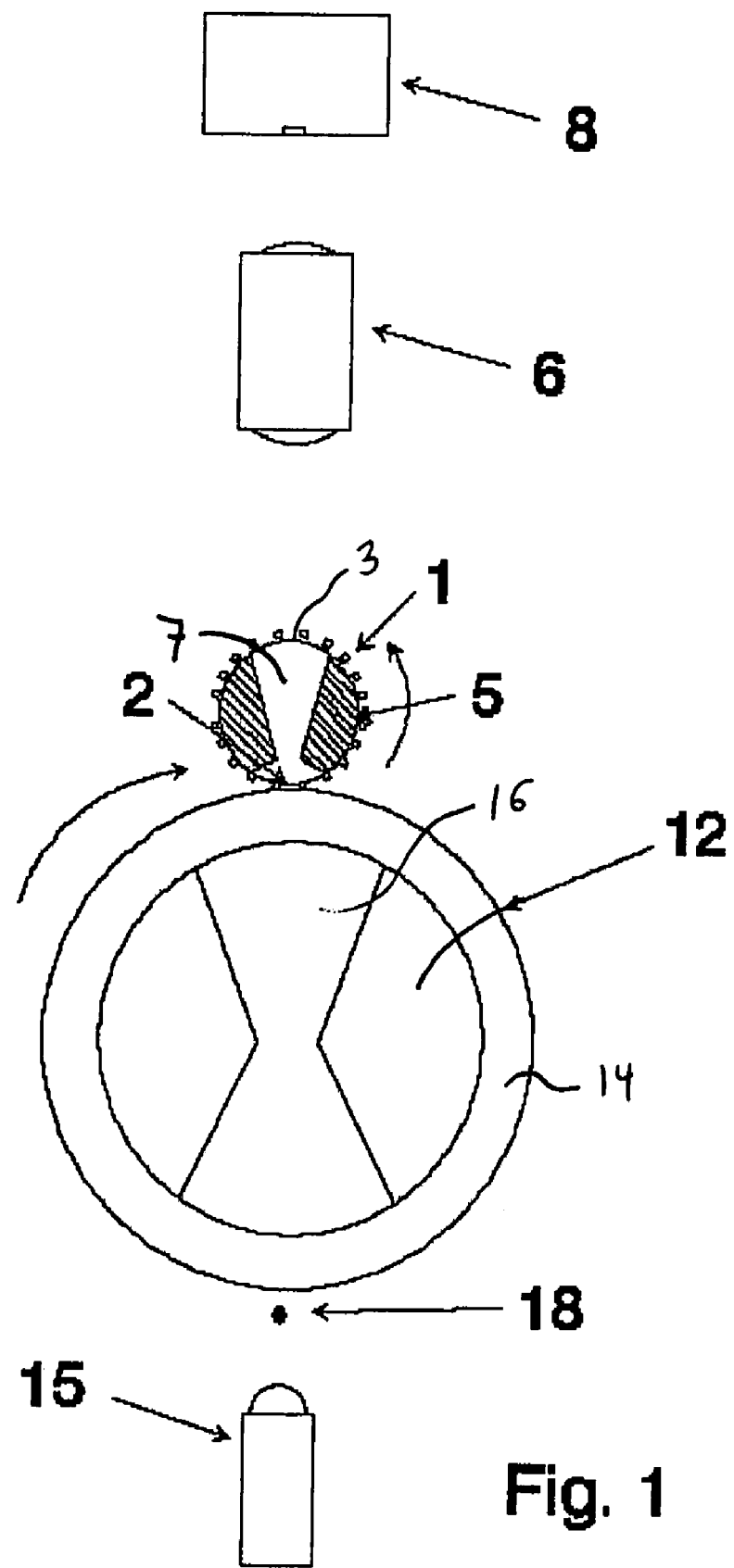
FIG. 1 schematically illustrates illumination of an inner sidewall of a stent in accordance with an embodiment of the invention.

FIG. 1 illustrates a first system that illuminates an inner diameter (ID) of a stent 1 while avoiding illumination of the outer diameter (OD) of the stent. Illumination on the OD creates substantial stray light degrading image quality and contrast. The stent 1 is mounted on a rigid slotted rod 5. A typical cardiovascular stent 1 has an inside diameter of about 1.5 millimeters and the slotted rod 5 has an outer diameter slightly less than that so the stent 1 does not collapse, but rotation of the stent 1 does not cause rotation of the slotted rod 5. Nominally, the outside diameter of the slotted rod 5 is 0.1 millimeter less than the inside diameter of the stent 1. A lens 6 has a depth of focus effective to image an interior wall 2 of the stent 1 onto a line scan camera 8 without also bringing the higher OD portion of the stent into focus. A drive device, such as rotatable drive wheel 12, contacts the stent 1 and is effective to rotate the stent around the slotted rod 5 at a desired rate. Light from a light source 15 passes through a translucent section 16 of drive wheel 12. An opaque projection 18 blocks excess light from the light source 15 that would otherwise provide too much contrast to line camera 8.

The slotted rod 5 is preferably formed from a rigid, opaque, material such as metal. The slotted rod is supported a fixed distance from the line scan camera 8 and the lens 6. The fixed in place slotted rod 5 has a slot 7 axially extending a length approximately equal to the viewing field of the lens, nominally 15 mm. The slot 7 enables line scan camera 8 to view through the slot 7 and take an image of the ID of the stent 1. While the slot may be cylindrical or any desired shape, an hourglass shape, or other shape effective to provide inwardly directed sidewalls effective to receive and reflect light from the light source, is preferred. The hourglass shape is formed by the slot having a maximum diameter at the surfaces of the rod and then a taper to a minimum at a point within the slotted rod. As shown in FIG. 1, the maximum diameters need not be the same on either side of the rod, nor need the rate of taper be similar such that the minimum diameter point is not necessarily at the center of the rod. Preferably, the minimum diameter point of the slotted rod 5 is located substantially closer to the bottom of the rod than the top so that this bottom portion functions like a reflector for light passing through the rotatable drive wheel 12 from source 15.

While the preferred slotted rod is formed from a rigid, opaque, material, fabricating the slotted rod from a clear or translucent material such as ceramic or quartz could be done as well. If light is directed from any angle, such a rod would itself become a glowing source of light. While this would accomplish the objective of providing a fixed arbor that provides illumination only on the inner diameter of a stent and not the outer diameter and keeps the ID being imaged at a precise position with respect to the camera, it would likely be a more difficult rod to produce and likely less durable in a manufacturing environment.

To rotate the stent 1 around the fixed rod 5, a motor driven wheel 12 that is preferably covered with a compliant, typically rubber, coating 14 is contacted with the stent 1. Preferably, the drive wheel 12 contacts with the stent at a point in alignment with slot 7. This provides a highly registered location for the stent image to be taken at a fixed distance from the lens 6 so as to accommodate the shallow depth of focus of a high numerical aperture (NA) lens 6. This numerical aperture is typically greater than 0.1. The driving wheel 12 includes an encoder that communicates with a motion controller that, for example, processes the stored values of a) the diameter of the drive wheel, b) the diameter of the stent and c) the resolution of the encoder to calculate the appropriate times to trigger the line camera to take a line and provide substantially square pixels.

It is preferable for the drive wheel 12 to have a substantially larger diameter than the stent 1, nominally by at least a factor of three to one. A section 16 of the drive wheel is substantially translucent to enable light to be transmitted through the drive wheel 12 and impinge on the slot 7 of the fixed slotted rod 5. By having the diameter of the drive wheel 12 substantially larger than the diameter of the stent, the stent may be rotated through 360° while contacting the substantially translucent section 16 of the drive wheel circumference. The inside surface of the slot 7 adjacent translucent section 16 has a concave shape along its axial length. This concave shape collects light and directs it onto the interior wall 2 of the stent 1. This approach avoids shining light on top outer diameter 3 of the stent. If illumination was delivered to the stent 1 from the opposing side adjacent camera 8 through the slot 7, there would be excessive stray light reflected into the lens from the top outer diameter 3 of the stent 1.

A line scan camera 8, such as the P2 6k manufactured by Dalsa Corporation of Waterloo, Ontario, Canada, is deployed to build up a line-by-line image of the interior sidewall 2 of the stent 1. To image the interior wall 2, a lens 6 of sufficiently high numerical aperture is employed to bring the interior sidewall of the stent 1 in clear focus, while leaving the nearer to lens 6 outer diameter 3 of the stent out of focus. The higher the numerical aperture, the shallower the depth of focus, therefore the preferred embodiment of this invention must hold the stent rigidly enough to keep the stent in good focus despite the generally shallow depth of focus of such a lens.

Exemplary of the numerical aperture and the resultant mechanical precision with which the stent 1 should be rotated in the field of view of the line scan camera 8, consider a typical cardiovascular stent with a 1.5 mm diameter. Assume that a camera and lens are looking down on the stent as it lies flat on a surface. Then for the top of the stent, the outer diameter, to be sufficiently out of focus so as to not in any way distort the image of the lower inner diameter the depth of focus must be, on the order of 5% of this 1.5 mm diameter or 0.075 mm. The actual geometry of the given stent does influence on this percentage. The denser the stent, the smaller the depth of field must be avoid a vingetting effect from the upper outer diameter, but 5% by length of the diameter seems a reasonable value for most stents. If we use the conventional formulas for depth of focus:

$$\text{Depth of Focus} = 1/NA^2, \qquad 1$$

then for a depth of focus of 75 microns=$1/NA^2$, NA=0.11. For a more dense part, a depth of focus closer to 25 microns is required. This yields a lens NA of 0.2. So then an aspect of this system is to mechanically rotate the stent under a line scan camera and precisely register the moving stent under the camera and lens to within 25 to 75 microns. One effective system for mechanical rotation is an ADRS-100 rotational stage manufactured by Aerotech Inc. of Pittsburgh, Pa. The rotating drive wheel 12 can be affixed to a mechanical stage and aligned to run true within the focus of the lens. The slotted rod 5 can be rigidly mounted to an assembly holding the lens 6 and camera 8 so that the slotted rod 5 can be properly aligned to the camera 8 and lens 6 and those three items can be constrained to maintain the ID of the stent in focus at all times. Also these three items can be all moved away from the drive wheel 12 as one mechanical package to allow loading and unloading of the slotted rod.

A further enhancement to the system is an opaque projection 18, such as a thin metal rod, disposed between the light source 15 and the drive wheel 12 substantially parallel to the fixed slotted rod 7. The opaque projection 18 blocks direct rays from the light source 15 that would otherwise travel unhindered towards the line scan camera 8. These unhindered rays would produce too much contrast between areas of material on the stent inner sidewalls and open areas. Such high contrast would cause camera blooming. An alternative method to avoiding excessive contrast is to split the light source into two separate elements each placed slightly off the main optical axis and aimed at the reflective areas at the bottom of the slotted tube.

Figure 2:
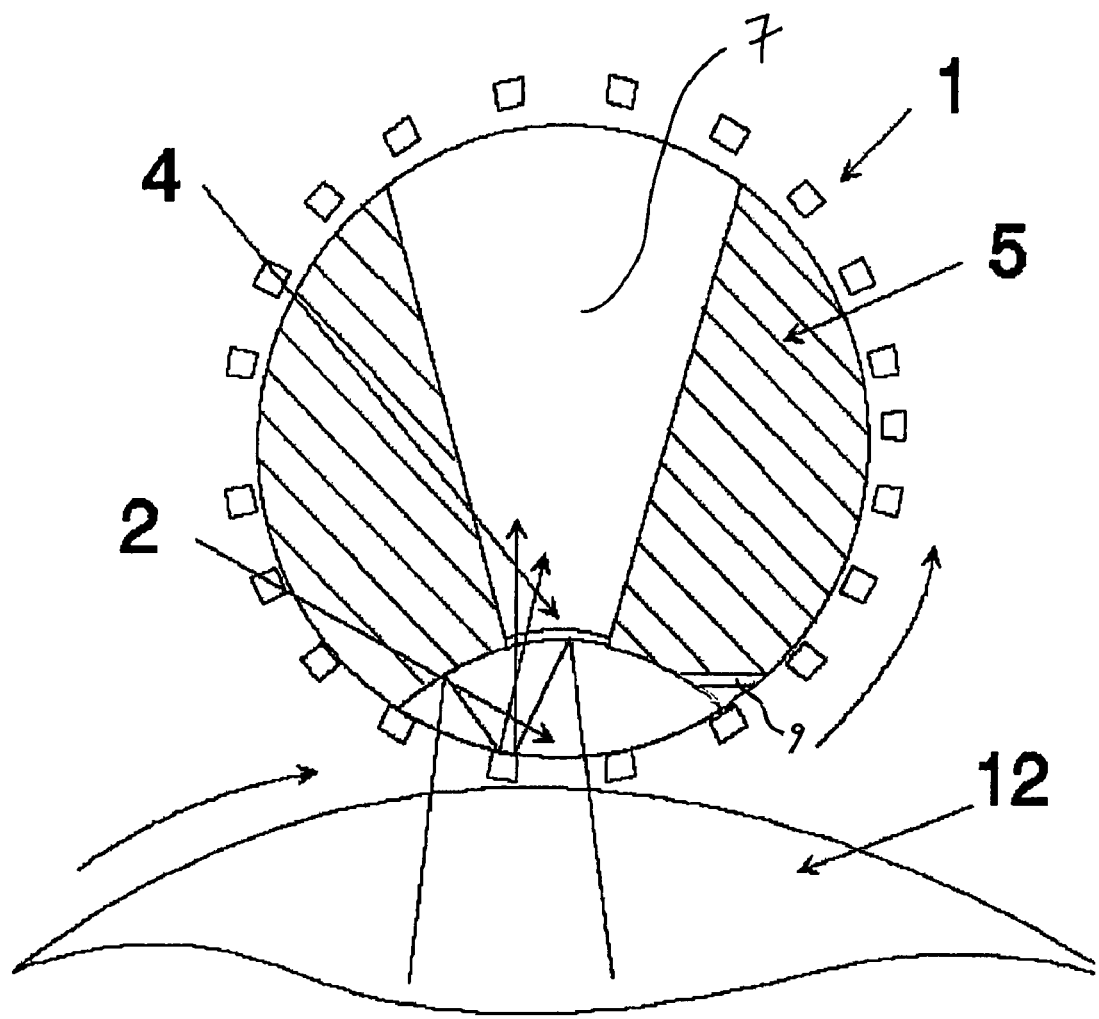
FIG. 2 shows a beamsplitter mounted inside a slotted rod to provide more complete illumination of the inner sidewall of the stent.

FIG. 2 shows a beamsplitter 4 mounted inside slotted rod 5 to provide more complete illumination to the interior wall 2 of stent 1. The beamsplitter 4, exemplary is a partially reflective mirror, within the slot 7 reflects some rays of the light transmitted through the drive wheel 12 onto the stent 1 and provides a more complete and uniform illumination. A slightly more complicated embodiment of this beamsplitter approach is to place the beamsplitter 4 in the slot 7 and add a second slot 9 in the rod 5 at right angles to the first slot solely for the purpose of delivering light to the beamsplitter 4 from the side.

Figure 3:
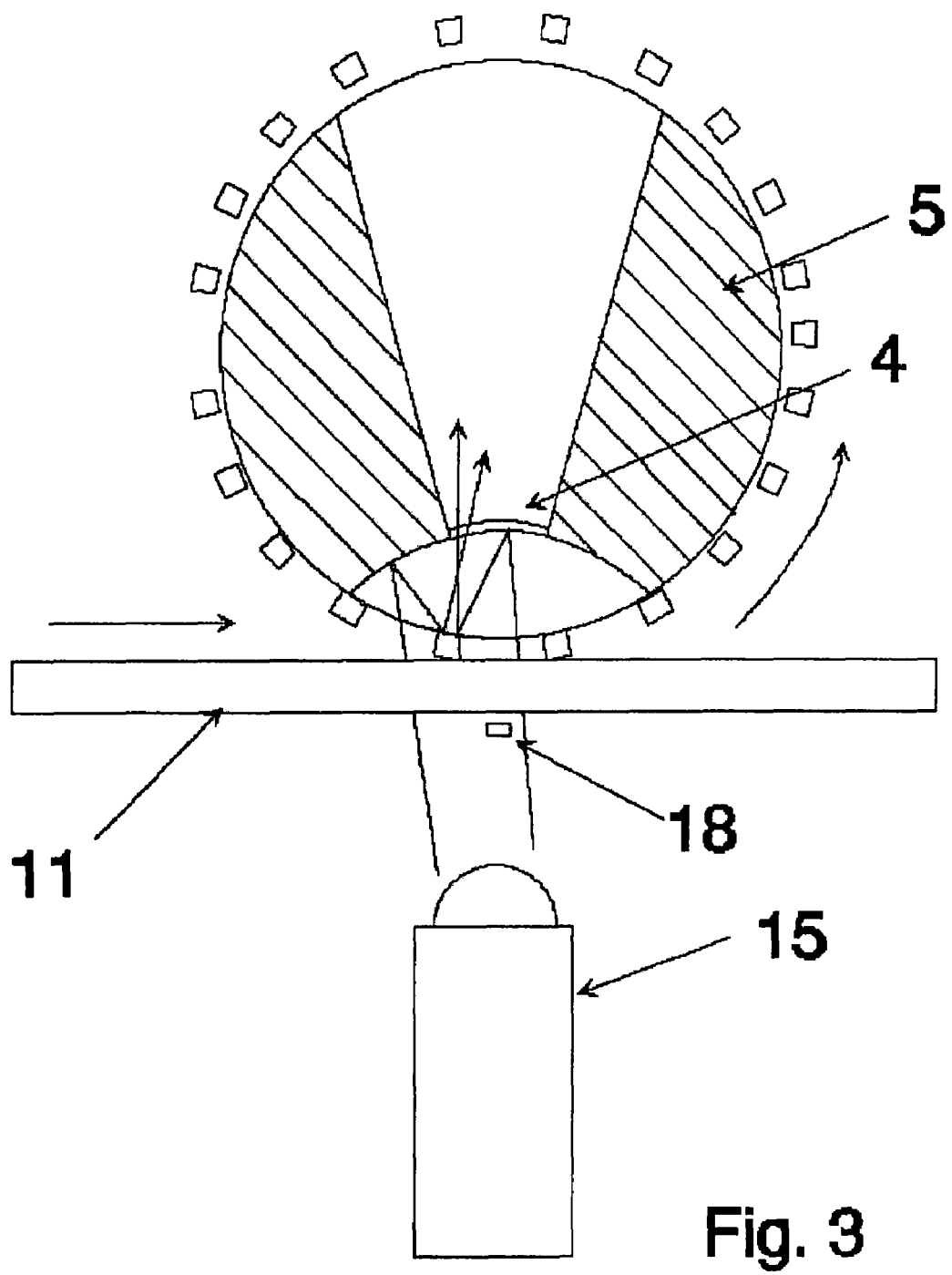
FIG. 3 shows an alternative embodiment utilizing a flat stage to drive the stent around slotted rod.

FIG. 3 shows an alternative embodiment where a flat stage, such as a clear plate, 11 is used to drive stent 1 around slotted rod 5. The flat stage 11 is capable of linear motion and replaces the rotating drive wheel. An advantage of this approach is that the calculation of the camera trigger pulse rate is simplified. A second advantage is that a flat glass element can be used and coated with a thin layer of compliant, translucent material to be the driver for stent rotation. One minor disadvantage may be the presence of a large mechanical object in close proximity to the rigid rod could complicate the loading and unloading of the stent for the operator.

Other means to rotate the stent under the high NA lens with the ability to hold the stent at the appropriate distance from the lens with sufficient precision can be suggested by those skilled in the art. We list here some of those approaches.

Figure 6:
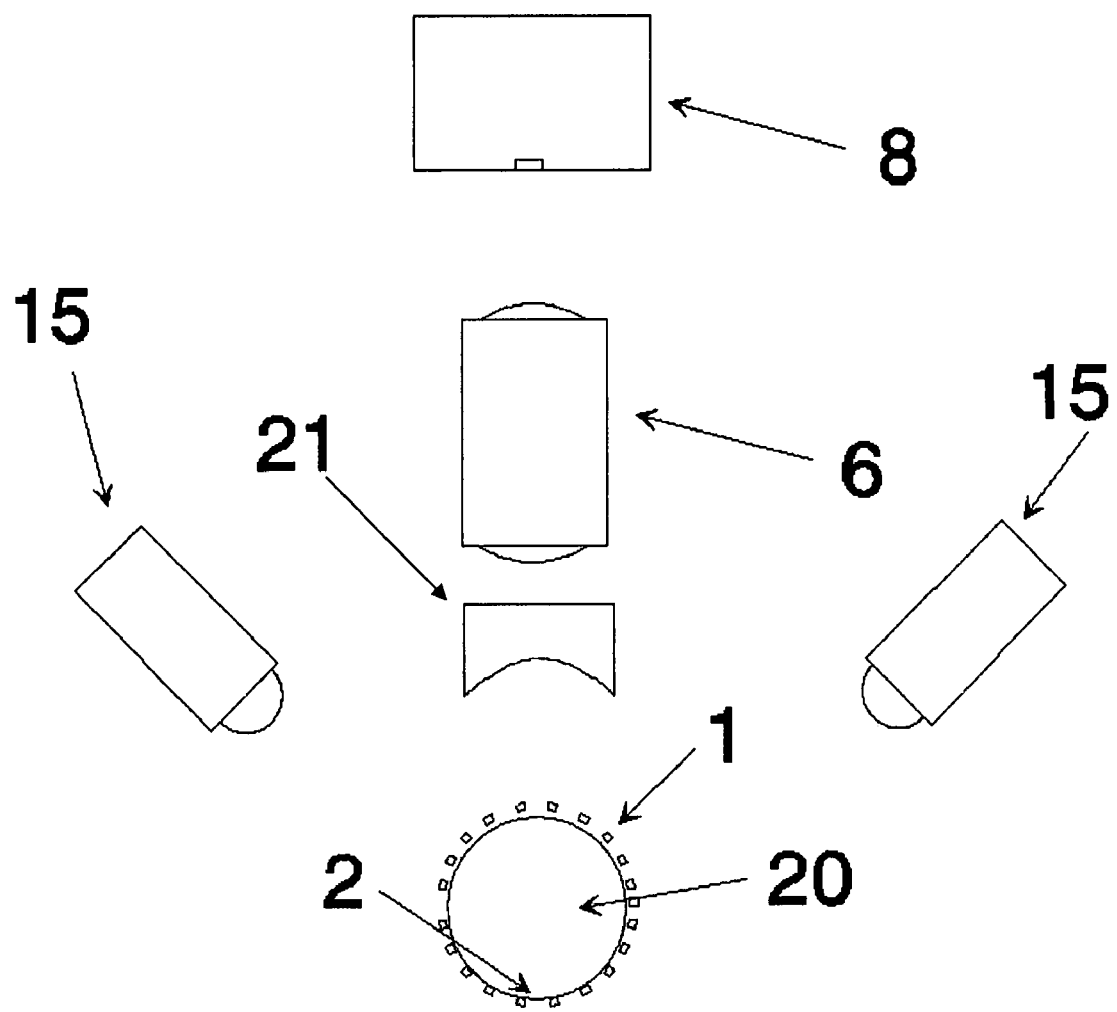
FIG. 6 shows another embodiment for rotating a stent.

FIG. 6 shows one method is to first place the stent on an optically clear cylindrical tube or within an optically clear tube 20. A cylindrical lens element 21 can be then used as part of the taking lens to compensate for any optical distortion caused by the rod or the tube. The clear rod or clear tube can then be rotated by a motor underneath the camera and lens and an image created. Light can then be directed from either side of the clear tube or rod at the ID of the stent by sources 15, thus avoiding the top of the OD of the stent and the inherent stray light caused by so illuminating this section of the stent.

Figure 4:
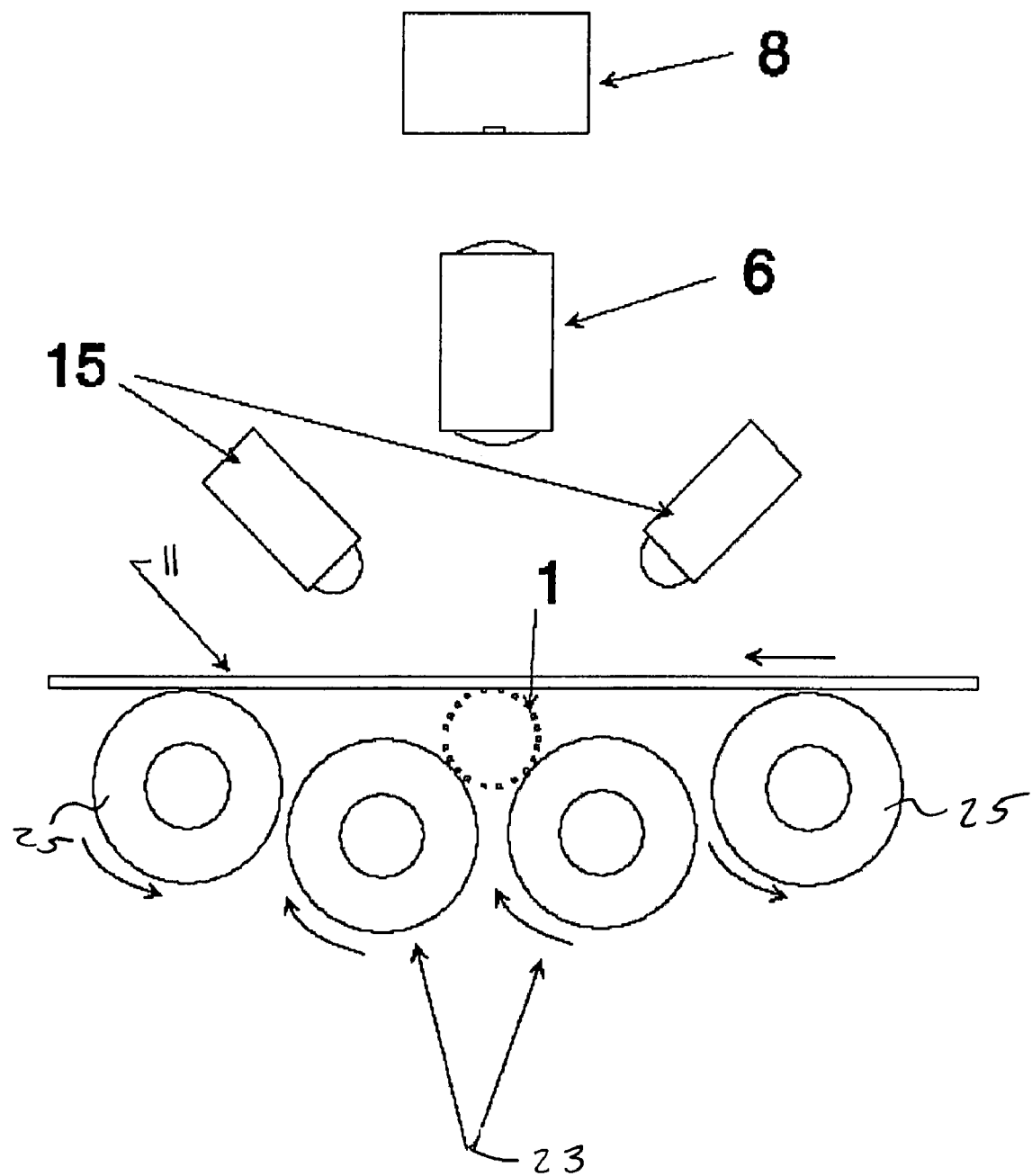
FIG. 4 shows another alternative utilizing two pairs of drive rollers that move a transparent stage while capturing and rotating the stent.

A commonly used drive mechanism to rotate a stent under a manual microscope is a pair of counter rotating rollers. Typically these rollers are at least three times the diameter of the stent so that the stent tends to nest between the rollers. After processing and manual handling, stents can sometimes take on a form that is not perfectly cylindrical. In such a case the interior sidewall of the stent would not rotate with the desired degree of precision required by the high NA lens described above. As shown in FIG. 4, to achieve this degree of placement precision a first pair of drive rollers 23 rotate the stent 1 under the view of line scan camera 8. A second pair of drive rollers 25 move transparent flat stage 11 synchronously and capture and rotate stent 1. The transparent flat stage, such as a moving glass cover slip, is supported by the second pair of drive rollers 25 that move it in synchronous motion with the rollers turning the stent. The second pair of drive rollers 25 is at an effective height with respect to the first pair of drive rollers 23 so that a slight compression is placed on the stent 1. This compression will keep the rotating stent well registered with respect to the depth of focus of the lens 6.

Figure 5:
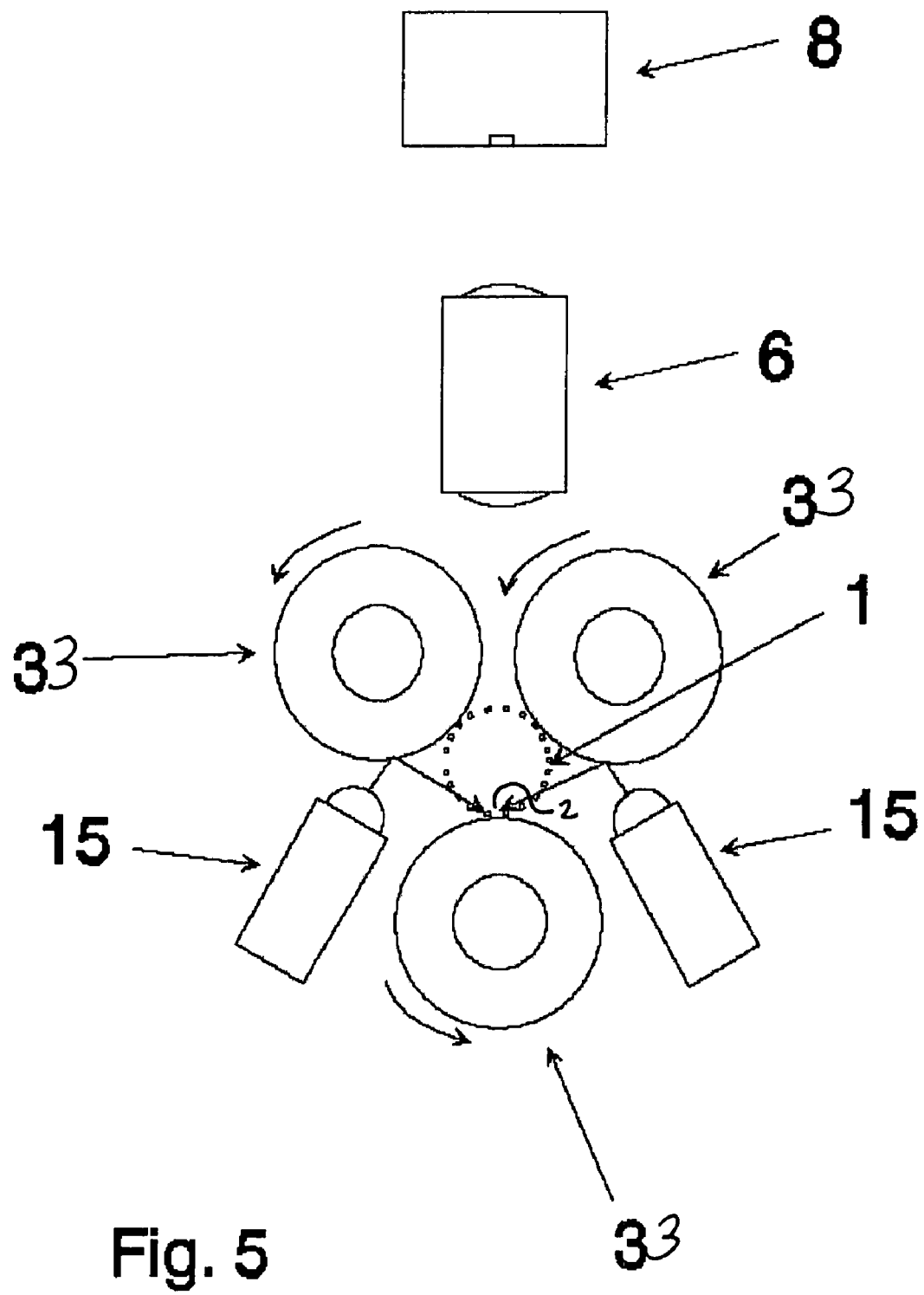
FIG. 5 shows another embodiment that utilizes three drive rollers to capture and rotate the stent.

An alternative roller approach is illustrated in FIG. 5. Three rollers 33 capture the stent 1 with each roller 33 exerting a slight pressure on the stent keeping it registered under the lens 6 to the proper precision. One or more light sources 15 reflect light off surfaces of the rollers 33 to illuminate the inner sidewall 2 of the stent. The geometry of the rollers 33 and the light sources 15 is such that none of the light from these sources impinges on the top OD surface of the part.

One or more embodiments of the present invention have been described. Nevertheless, it will be understood that various modifications may be made without departing from the spirit and scope of the invention. Accordingly, other embodiments are within the scope of the following claims.

We claim:

1. An optical system effective to illuminate and scan an interior wall of an object having an interior bore, comprising:
    a light source;
    an object support disposed between said light source and an image taking lens, said object support being a rod having a first light conducting portion extending therethrough with a beam splitter effective to reflect light from said light source to said interior wall disposed within said first light conducting portion, said object support further having a second light conducting portion disposed generally perpendicularly to said first light conducting portion that is effective to transmit light to said beam splitter for reflection to said interior wall on to said image taking lens;

said image taking lens disposed between said object support and a line scan camera, said image taking lens having a depth of focus sufficiently shallow that an exterior wall of said object is out of focus when an opposing interior wall of said object is in focus, and wherein said interior bore and said light conducting portion are in axial alignment with a center optical axis of said image taking lens; and a drive mechanism engaging said object without impacting said axial alignment with a rotary encoder engaging said drive mechanism and driving an electric circuit capable of triggering said line scan camera in response to rotation of the object, thereby building a line by line image of said interior bore.

2. The optical system of claim 1 wherein said drive mechanism is a rotating wheel that contacts said object.

3. The optical system of claim 2 wherein said rotating wheel includes a light conducting through hole in axial alignment with said interior bore.

4. The optical system of claim 2 wherein said rotating wheel has a diameter greater than a diameter of said object.

5. The optical system of claim 1 wherein said object is a stent.

6. The optical system of claim 1 wherein said rod is at least partially transparent.

7. The optical system of claim 1 wherein said rod is formed from a material selected from the group consisting of ceramic and quartz.

* * * * *